United States Patent
Kim

(10) Patent No.: US 7,312,268 B2
(45) Date of Patent: Dec. 25, 2007

(54) WATER-ABSORBENT CARBOXYL-CONTAINING POLYMERS WITH LOW MONOMER CONTENT

(75) Inventor: Young-Sam Kim, Midland, MI (US)

(73) Assignee: Stockhausen GmbH, Krefeld (DE)

( * ) Notice: Subject to any disclaimer, the term of this patent is extended or adjusted under 35 U.S.C. 154(b) by 312 days.

(21) Appl. No.: 10/469,664

(22) PCT Filed: Jun. 26, 2002

(86) PCT No.: PCT/US02/20573

§ 371 (c)(1),
(2), (4) Date: Feb. 23, 2004

(87) PCT Pub. No.: WO03/002618

PCT Pub. Date: Jan. 9, 2003

(65) Prior Publication Data

US 2004/0138362 A1     Jul. 15, 2004

Related U.S. Application Data

(60) Provisional application No. 60/302,330, filed on Jun. 29, 2001.

(51) Int. Cl.
C08K 3/10 (2006.01)

(52) U.S. Cl. ........... 524/403; 524/444; 524/556

(58) Field of Classification Search ........ 524/403, 524/444, 556
See application file for complete search history.

(56) References Cited

U.S. PATENT DOCUMENTS

| | | | |
|---|---|---|---|
| 4,286,082 A | 8/1981 | Tsubakimoto et al. | 526/240 |
| 4,295,987 A | 10/1981 | Parks | 252/194 |
| 4,303,771 A | 12/1981 | Wagner et al. | 526/125 |
| 4,340,706 A | 7/1982 | Obayashi et al. | 526/207 |
| 4,506,052 A | 3/1985 | Furukawa et al. | 524/357 |
| 4,610,678 A | 9/1986 | Weisman et al. | 604/368 |
| 4,654,039 A | 3/1987 | Brandt et al. | 604/368 |
| 4,659,793 A | 4/1987 | Yang | 526/91 |
| 4,666,983 A | 5/1987 | Tsubakimoto et al. | 525/119 |
| 4,734,478 A | 3/1988 | Tsubakimoto et al. | 527/300 |
| RE32,649 E | 4/1988 | Brandt et al. | 604/368 |
| 4,766,173 A | 8/1988 | Bailey et al. | 524/819 |
| 4,929,717 A | 5/1990 | Chmelir | 528/490 |
| 4,962,172 A | 10/1990 | Allen et al. | 526/318.42 |
| 5,145,906 A | 9/1992 | Chambers et al. | 524/732 |
| 5,147,956 A | 9/1992 | Allen | 526/318.42 |
| 5,229,488 A | 7/1993 | Nagasuna et al. | 528/487 |
| 5,258,473 A * | 11/1993 | Niessner et al. | 526/78 |
| 5,342,899 A | 8/1994 | Graham et al. | 525/301 |
| 5,453,323 A * | 9/1995 | Chambers et al. | 428/402 |
| 5,506,324 A | 4/1996 | Gartner et al. | 526/318.41 |
| 5,629,377 A * | 5/1997 | Burgert et al. | 524/832 |
| 5,744,564 A | 4/1998 | Stanley et al. | 526/317.1 |
| 5,866,678 A | 2/1999 | Kajikawa et al. | 528/487 |
| 5,994,440 A | 11/1999 | Staples et al. | 524/377 |
| 6,277,772 B1 * | 8/2001 | Gancet et al. | 442/327 |
| 6,323,252 B1 | 11/2001 | Gartner et al. | 521/149 |
| 6,455,600 B1 * | 9/2002 | Hahnle et al. | 521/63 |
| 6,716,895 B1 * | 4/2004 | Terry | 523/122 |
| 6,726,936 B1 * | 4/2004 | Asano et al. | 424/618 |
| 2004/0157971 A1 * | 8/2004 | Kim | 524/403 |

FOREIGN PATENT DOCUMENTS

| | | |
|---|---|---|
| EP | 505163 | 3/1992 |
| GB | 2119384 | 11/1983 |
| JP | 09030901 A * | 2/1997 |
| WO | WO98/49221 | 11/1998 |
| WO | WO 9965317 A1 * | 12/1999 |
| WO | WO 0141819 * | 6/2001 |

OTHER PUBLICATIONS

Derwent Abstract of DE 2,706,135, E. Barthell, et al., Sep. 1, 1993.
U.S. Appl. No. 10/471,874; Young-Sam, Kim; Superabsorbent Carboxyl-Containing Polymers With Odor Control Properties And Method For Preparation., Jun. 26, 2002.
U.S. Appl. No. 10/480,328; Young-Sam, Kim; Superabsorbent Carboxyl-Containing Polymers With Odor Control Properties And Method For Preparation., Jun. 26, 2002.

* cited by examiner

*Primary Examiner*—David W. Wu
*Assistant Examiner*—Satya Sastri
(74) *Attorney, Agent, or Firm*—Smith Moore LLP

(57) ABSTRACT

A water absorbent polymer with reduced residual monomer content is prepared using silver ions and/or colloidal silver.

23 Claims, No Drawings

WATER-ABSORBENT CARBOXYL-CONTAINING POLYMERS WITH LOW MONOMER CONTENT

CROSS REFERENCE TO RELATED APPLICATIONS

This application is a 371 of PCT/US02/20,573 filed Jun. 26, 2002, which claims the benefit of U.S. Provisional Application Ser. No. 60/302,330, filed Jun. 29, 2001.

BACKGROUND OF THE INVENTION

This invention relates to water-absorbent carboxyl-containing polymers having a low residual monomer content and a process for their preparation.

Water-absorbent polymers, also referred to as superabsorbent polymers or aqueous fluid absorbent polymers, are primarily used in personal care products which absorb body fluids, for example, baby diapers, adult incontinence products and feminine hygiene products. In such applications, superabsorbent polymer particles are incorporated into absorbent structures that contain synthetic and/or natural fiber or paper based, woven and nonwoven structures, or toughened masses of fibers, such as fluff pads. The materials used in such structures can quickly absorb aqueous fluids and distribute them throughout the whole absorbent structure. The structures, in the absence of superabsorbent polymers, have limited absorption capacity, are bulky due to the large amount of material needed to provide acceptable absorption capacity, and do not retain fluid under pressure. A means for improving the absorbency and fluid retention characteristics of such absorbent structures is to incorporate superabsorbent polymer particles that imbibe fluids to form a swollen hydrogel material.

The superabsorbent polymer particles quickly absorb fluids and retain such fluids to prevent leakage and give the absorbent structure a "dry feel" even when wetted. See U.S. Pat. No. 4,610,678 for examples of such polymers. See also U.S. Pat. No. 4,654,039 and Re. No. 32,649, which disclose a process for the preparation of superabsorbent polymers and the use of known crosslinking agents for such polymers, and also U.S. Pat. Nos. 4,295,987 and 4,303,771. A variation of the basic process is taught in GB Patent 2,119,384, which discloses a post polymerization surface crosslinking process in which the previously polymerized absorbent polymer powder is mixed with crosslinkers, preferably polyalcohols, a solvent and water, to coat the polymer surface and is heated to temperatures in the range of 90 to 300° C. to crosslink the surface. U.S. Pat. No. 5,506,324 discloses superabsorbent polymer particles comprising polymers containing carboxyl moieties which are crosslinked using $C_{2-10}$ polyhydric hydrocarbons which are ethoxylated with from 2 to 8 ethylene oxide units per hydroxyl moiety of the polyhydric hydrocarbon wherein the hydroxyl moiety at the end of each ethylene oxide chain is esterified with a $C_{2-10}$ unsaturated carboxylic acid or ester thereof. In a preferred embodiment, the superabsorbent polymer particles are subjected to a heat-treatment process after drying and sizing the particles.

A basic problem with commercially available water-absorbent polymer has been the presence of residual monomers. A water-absorbent polymer product with reduced residual monomer content is highly desired. Various methods to lower the residual monomer content are known in the art.

European Patent Publication 505 163 relates to a method for reducing residual (meth)acrylic acid present in poly (acrylic acid) water-absorbent gel polymers which comprises treating these polymers with a combination of a surfactant having a certain HLB and a vinylic addition compound that can react with a vinylic double bond. Examples of the vinylic addition compound include sulfites and bisulfites. The surfactant and the vinylic addition compound may be used in admixture with oxidizing anions, such as peroxodisulfate and peroxide. An aqueous solution of the additives is mixed with the water-absorbent polymer in the form of swollen gels or beads or dry polymer. The presence of surfactants is believed to negatively affect the liquid distribution when the polymer is wetted. In addition, vinyl addition compounds like sulfites and bisulfites generally cause offensive odor problems during processing.

U.S. Pat. No. 5,629,377 discloses a process for preparing water-absorbent polymer particles comprising polymerizing unsaturated carboxyl-containing monomers in the presence of a chlorine- or bromine-containing oxidizing agent to form a hydrogel which is then heated at a temperature of from 170° C. to 250° C., preferably of from 210° C. to 235° C. Alternatively, the chlorine- or bromine-containing oxidizing agent may be added to the polymerized hydrogel. The method is effective for improving absorbency, for example, centrifuge capacity and absorbency under load (AUL), while keeping the amount of residual monomers at an acceptable level. However, the high heat treat temperature needed to activate the chlorine- or bromine-containing oxidizing agent is detrimental for various reasons, including high energy usage and loss of moisture.

U.S. Pat. No. 4,659,793 teaches that very small amounts of certain metal ions ($Zn^{2+}$, $Co^{3+}$, $Co^{2+}$, $Cu^{2+}$, $Mo^{2+}$, $Fe^{3+}$, $Fe^{2+}$, $Cr^{3+}$, $Ni^{2+}$, $Ce^{3+}$ and $Ce^{2+}$) promote the copolymerization of ethylenically unsaturated dicarboxylic acid monomers, especially maleic acid, and $\alpha,\beta$-ethylenically unsaturated monomers having carboxyl or sulfonic acid groups, such as (meth)acrylic acid or 2-acrylamido-2-methyl propane sulfonic acid, whereby the amount of unreacted dicarboxylic acid monomer is significantly reduced. The metal ions are added to the monomer mixture. The resulting copolymer is not described as a superabsorbent polymer but is useful in antiscalants, dispersants, detergent additives, deflocculants etc.

Numerous other methods are known to reduce the amount of residual monomers in superabsorbent materials, for example, the use of sulfites, bisulfites, ammonia, amines, amino acids like cystein and lysine, sulfurous acid, phosphorous acid, pyrophosphorous acid, hypophosphorous acid, thiosulfuric acid, hydroxylamine or a salt thereof, and ascorbic acid (see U.S. Pat. Nos. 5,229,488, 5,866,678, 4,766,173, and 4,929,717).

The various methods taught in the prior art use additional non-reactive additives in addition to the reactive agents mentioned above and/or additional mixing measures to improve the distribution of the reactive agents. The non-reactive additives may be substances that can modify hydrogel particles, and may be not only surfactants but also, for example, organic solvents, mineral oils and very fine inorganic or organic particles like silicon dioxide, aluminum dioxide, zeolite or poly(methyl methacrylate) particles. The use of such additives complicates the manufacturing process, which then is more time-consuming and therefore less economical. In addition, the use of additives such as surfactants and very fine powders may adversely affect absorbence and liquid distribution.

It would be highly desirable to provide a novel method for the preparation of water-absorbent polymers having a low residual monomer level, which method would eliminate the above-mentioned disadvantages.

SUMMARY OF THE INVENTION

This invention relates to a process for the preparation of a water-absorbent polymer, which comprises
(I) polymerizing a polymerization mixture comprising:
  (a) one or more ethylenically unsaturated carboxyl-containing monomers,
  (b) one or more crosslinking agents,
  (c) optionally one or more comonomers copolymerizable with the carboxyl-containing monomer, and
  (d) a polymerization medium to form a crosslinked hydrogel,
(II) committing the hydrogel to create particles and
(III) drying the hydrogel; wherein silver ions or colloidal silver are added in at least one of the following steps:
(i) to the polymerization mixture prior to or during step (I), or
(ii) to the hydrogel prior to, during or after the comminution step (II) but prior to substantial drying of the hydrogel in step (III).

Another aspect of the invention is a water-absorbent polymer containing silver ions or colloidal silver prepared by the process of this invention. This invention also concerns an absorbent structure comprising water-absorbent polymer of this invention and at least one of a woven or non-woven structure of paper, synthetic fibers, natural fibers or a combination of these.

The key element of the present invention is the addition of silver ions or colloidal silver in the process for the preparation of the water-absorbent polymer. The presence of silver ions or colloidal silver in the polymer product prior to heating was surprisingly found to result in reduced residual monomer content, regardless of how the silver ions were incorporated into the water-absorbent polymer particles. The present invention does not comprise technically complicated and time-consuming process steps and productivity is not reduced compared to processes not employing silver ions.

DETAILED DESCRIPTION OF THE INVENTION

The water-absorbent polymer of the present invention after drying, but before heat treatment, has a low residual monomer content, preferably less than 300 ppm and more preferably less than 200, all based on the weight of dry polymer. The heat-treated water-absorbent polymer of the present invention also has a low residual monomer content, preferably less than 500 ppm and more preferably less than 400, based on the weight of dry polymer.

An important aspect of the present invention is the addition of silver ions or colloidal silver to the process for preparing water-absorbent polymer. The amount of silver ions or colloidal silver added preferably ranges from 1 to 100,000 ppm and more preferably from 1 to 10,000 ppm, even more preferably from 10 to 1,000 ppm and most preferably from 25 to 1,000 ppm, all based on weight of dry polymer.

The silver ions may be added as one or more dry silver salts or as a solution of one or more silver salts. The solution may be an aqueous solution, a non-aqueous organic solution or a solution in a mixture of water and organic solvent, with an aqueous solution being preferred. An aqueous solution may also be prepared by complexation of water-insoluble silver salts.

The silver salts are applied to the superabsorbent polymer either in powdered salt form or as a solution or suspension. The solution can be aqueous, organic, or a mixture of these. Water-soluble silver salts, which are termed "soluble silver salts" in the present application, are the preferred source of silver ions. The solubility of various silver salts generally can be improved by acidifying them, dissolving them in alkalis, dissolving them in organic solvent, dissolving them at elevated temperatures, and/or intensive mixing during the dissolution process. The degree of solubility of the silver salt is not particularly critical. The soluble silver salts preferably have a solubility in pH neutral water at room temperature of not less than 0.0016 g per liter. More preferably, the soluble silver salts have a solubility in water at room temperature of not less than 1 g per liter. Most preferably, the soluble silver salts have a solubility of not less than 10 g per liter.

Examples of silver salts include, for example silver acetate, silver acetylacetonate, silver azide, silver acetylide, silver arsenate, silver benzoate, silver bifluoride, silver monofluoride, silver fluoride, silver borfluoride, silver bromate, silver bromide, silver carbonate, silver chloride, silver chlorate, silver chromate, silver citrate, silver cyanate, silver cyanide, silver-(cis,cis-1,5-cyclooctadiene)-1,1,1,5,5,5,-hexafluoroacetylacetonate, silver dichromate tetrakis-(pyridine)-complex, silver diethyldithiocarbamate, silver(I) fluoride, silver(II) fluoride, silver-7,7-dimethyl-1,1,1,2,2,3,3,-heptafluor-4,6-octandionate, silver hexafluoroantimonate, silver hexafluoroarsenate, silver hexafluorophosphate, silver iodate, silver iodide, silver isothiocyanate, silver potassium cyanide, silver lactate, silver molybdate, silver nitrate, silver nitrite, silver(I) oxide, silver(II) oxide, silver oxalate, silver perchlorate, silver perfluorobutyrate, silver perfluoropropionate, silver permanganate, silver perrhenate, silver phosphate, silver picrate monohydrate, silver propionate, silver selenate, silver selenide, silver selenite, silver sulfadiazine, silver sulfate, silver sulfide, silver sulfite, silver telluride, silver tetrafluoroborate, silver tetraiodomecurate, silver tetratungstenate, silver thiocyanate, silver-p-toluensulfonate, trifluoromethanesulfonic acid silver salt, trifluoroacetic acid silver salt, and silver vanadate. Mixtures of various silver salts can also be used. The preferred silver salts are silver acetate, silver benzoate, silver bromate, silver chlorate, silver lactate, silver molybdate, silver nitrate, silver nitrite, silver(I) oxide, silver perchlorate, silver permanganate, silver selenate, silver selenite, silver sulfadiazine, and silver sulfate. The most preferred silver salts are silver acetate and silver nitrate.

Examples of water-insoluble silver salts include by silver halides including silver chloride, bromide, and other silver salts having a very low solubility in water. They advantageously are added together with agents that undergo complexation with the silver ion. Alkali metal thiosulfate, ammonia, chloride and alkali metal cyanides are exemplary complexing agents for the water-insoluble silver chloride and silver bromide. By reacting silver halides and the complexing agents the corresponding silver complex ion is formed, for example, silver thiosulfate complex ion, silver chloride complex ion, silver amino complex ion and silver cyanide complex ion, where the complexing agents are sodium thiosulfate, sodium chloride, ammonia and sodium cyanide, respectively. The most preferred silver ion complexing agents are alkali metal thiosulfate salts including sodium and potassium and sodium chloride. Silver thiosulfate complex can be formed by simply reacting silver chloride and sodium thiosulfate in water at ambient temperature without heating. Sodium chloride needs a higher reaction temperature for forming silver chloride complex ions. The molar ratio of silver cations from the silver halide to thiosulfate anions from the sodium thiosulfate preferably ranges from 0.001 to 100. The aqueous solution of silver complex ions may be heterogeneous, that is, silver salts can be dissolved by incomplete complexation, based on the molar ratio of silver cations to complexing anions.

The water-absorbent, water-insoluble polymers advantageously are derived from one or more ethylenically unsaturated carboxylic acids, ethylenically unsaturated carboxylic acid anhydrides or salts thereof. Additionally, the polymers may include comonomers known in the art for use in superabsorbent polymers or for grafting onto the superabsorbent polymers including comonomers such as an acrylamide, an acrylonitrile, a vinyl pyrrolidone, a vinyl sulphonic acid or a salt thereof, a cellulosic monomer, a modified cellulosic monomer, a polyvinyl alcohol or a starch hydrolyzate. If used, the comonomer comprises up to 25 percent by weight of the monomer mixture.

Preferred unsaturated carboxylic acid and carboxylic acid anhydride monomers include the acrylic acids typified by acrylic acid, methacrylic acid, ethacrylic acid, α-chloroacrylic acid, α-cyano acrylic acid, β-methyl acrylic acid (crotonic acid), α-phenyl acrylic acid, β-acryloyloxy propionic acid, sorbic acid, α-chloro sorbic acid, angelic acid, cinnamic acid, p-chloro cinnamic acid, beta-styrenic acrylic acid (1-carboxy-4-phenyl butadiene-1,3), itaconic acid, citraconic acid, mesaconic acid, glutaconic acid, maleic acid, fumaric acid and maleic acid anhydride. More preferably the starting monomer is acrylic acid, methacrylic acid, or a salt thereof with acrylic acid or a salt thereof being most preferred. The use herein of the prefix "(meth)" with generic terms, such as, for example, "acrylic acid", or "acrylate" is meant to broaden the terms to include both acrylate and methacrylate species. Thus, the term "(meth)acrylic acid monomer" includes acrylic acid and methacrylic acid.

Preferably, 25 mole percent or greater of the carboxylic acid units of the hydrophilic polymer are neutralized with base, even more preferably 50 percent or greater and most preferably 65 percent or greater. This neutralization may be performed after completion of the polymerization. In a preferred embodiment the starting monomer mix has carboxylic acid moieties that are neutralized to the desired level prior to polymerization. The final polymer or the starting monomers may be neutralized by contacting them with a salt forming cation. Such salt-forming cations include alkaline metal, ammonium, substituted ammonium and amine based cations. Preferably, the polymer is neutralized with an alkali metal hydroxide such as, for example, sodium hydroxide or potassium hydroxide, or an alkali metal carbonate such as, for example, sodium carbonate or potassium carbonate.

The water-absorbent polymers of the invention are lightly crosslinked to make them water-insoluble. Vinyl, non-vinyl, or dimodal crosslinkers can be employed, either alone, as mixtures, or in various combinations. Polyvinyl crosslinkers commonly known in the art for use in superabsorbent polymers advantageously are employed. Preferred compounds having at least two polymerizable double bonds include: di- or polyvinyl compounds such as divinyl benzene, divinyl toluene, divinyl xylene, divinyl ether, divinyl ketone and trivinyl benzene; di- or polyesters of unsaturated mono- or polycarboxylic acids with polyols, such as di- or tri-(meth)acrylic acid esters of polyols such as ethylene glycol, diethylene glycol, triethylene glycol, tetra ethylene glycol, propylene glycol, dipropylene glycol, tri propylene glycol, tetra propylene glycol, trimethylol propane, glycerin, polyoxyethylene glycols and polyoxypropylene glycols; unsaturated polyesters that can be obtained by reacting any of the above-mentioned polyols with an unsaturated acid such as maleic acid; di- or polyesters of unsaturated mono- or polycarboxylic acids with polyols derived from reaction of $C_2$-$C_{10}$ polyhydric alcohols with 2 to 8 $C_2$-$C_4$ alkylene oxide units per hydroxyl group, such as trimethylol propane hexaethoxyl triacrylate; di- or tri-(meth)acrylic acid esters that can be obtained by reacting polyepoxide with (meth) acrylic acid; bis(meth) acrylamides such as N,N-methylenebisacrylamide; carbamyl esters that can be obtained by reacting polyisocyanates such as tolylene diisocyanate, hexamethylene diisocyanate, 4,4'-diphenyl methane diisocyanate and NCO-containing prepolymers obtained by reacting such diisocyanates with active hydrogen atom-containing compounds with hydroxyl group-containing monomers, such as di-(meth)acrylic acid carbamyl esters obtainable by reacting the above-mentioned diisocyanates with hydroxyethyl(meth)acrylate; di- or poly(meth)allyl ethers of polyols such as alkylene glycols, glycerol, polyalkylene glycols, polyoxyalkylene polyols and carbohydrates such as polyethylene glycol diallyl ether, allylated starch, and allylated cellulose; di- or poly-allyl esters of polycarboxylic acids, such as diallyl phthalate and diallyl adipate; and esters of unsaturated mono- or polycarboxylic acids with mono (meth)allyl ester of polyols, such as allyl methacrylate or (meth)acrylic acid ester of polyethylene glycol monoallyl ether.

Among the preferred classes of crosslinkers are bis(meth) acrylamides; allyl(meth)acrylates; di- or poly-esters of (meth)acrylic acid with polyols such as diethylene glycol diacrylate, trimethylol propane triacrylate, and polyethylene glycol diacrylate; and di- or polyesters of unsaturated mono- or poly-carboxylic acids with polyols derived from reaction of $C_1$-$C_{10}$ polyhydric alcohols with 2 to 8 $C_2$-$C_4$ alkylene oxide units pen hydroxyl group, such as ethoxylated trimethylol propane triacrylate. More preferably the crosslinking agents correspond to Formula 1

$$R^1(—(R^2O)_n—C(O)R^3)_x \qquad \text{Formula 1}$$

wherein:

$R^1$ is a straight- on branched-chain polyalkoxy radical with 1 to 10 carbon atoms, optionally substituted with one on more oxygen atoms in the backbone, having x valences;

$R^2$ is independently in each occurrence an alkylene group of 2 to 4 carbon atoms;

$R^3$ is independently in each occurrence a straight- or branched-chain alkenyl moiety with 2 to 10 carbon atoms; and n is a number from 1 to 20;

x is a number from 2 to 8.

In the most preferred embodiment the polyvinyl crosslinker corresponds to Formula 1 wherein $R^1$ is derived from trimethylolpropane, $R^2$ is ethylene —($CH_2CH_2$)—, $R^3$ is vinyl—($CH$=$CH_2$), the average value of n is from 2 to 6, and x is 3. The most preferred polyvinyl crosslinker is highly ethoxylated trimethylolpropane triacrylate, containing an average of 15 to 16 ethoxyl groups per molecule of trimethylolpropane. Crosslinkers corresponding to Formula 1 are available from Craynor under the trademark Craynor and from Sartomer under the trademark Sartomer. Generally, the crosslinkers described by Formula 1 are found as a mixture of materials described by the formula and by-products resulting from the preparation process. Mixtures of polyvinyl crosslinkers can be employed.

The non-vinyl crosslinkers of this invention are agents having at least two functional groups capable of reacting with the carboxyl groups of the polymer, and include materials such as glycerin, polyglycols, ethylene glycol digylcidyl ether, and diamines. Many examples of these agents are given in U.S. Pat. Nos. 4,666,983 and 4,734,478 which teach the application of such agents to the surface of absorbent polymer powder followed by heating to crosslink surface chains and improve absorption capacity and absorption rate. Additional examples are given in U.S. Pat. No. 5,145,906 which teaches post-crosslinking with such agents. In the current invention, the non-vinyl crosslinkers advantageously are added homogeneously to the polymerization mixture at the start of the process. Preferred non-vinyl crosslinkers include hexane diamine, glycerin, ethylene glycol diglycidyl ether, ethylene glycol diacetate, polyethylene glycol 400, polyethylene glycol 600, and polyethylene glycol 1000. Examples of more preferred non-vinyl crosslinkers include polyethylene glycol 400 and polyethylene glycol 600. Mixtures of non-vinyl crosslinkers can be employed.

The dimodal crosslinkers that can be employed in the process of this invention are agents that have at least one polymerizable vinyl group and at least one functional group capable of reacting with carboxyl groups. To distinguish these from normal vinyl crosslinkers, we call them "dimodal crosslinkers," because they use two different modes of reaction to form a crosslink. Examples of dimodal crosslinkers include hydroxyethyl methacrylate, polyethylene glycol monomethacrylate, glycidyl methacrylate, and allyl glycidyl ether. Many examples of these type of agents are given in U.S. Pat. Nos. 4,962,172 and 5,147,956 which teach the manufacture of absorbent films and fibers by (1) the preparation of linear copolymers of acrylic acid and hydroxyl containing monomers, (2) forming solutions of these copolymers into the desired shapes, and (3) fixing the shape by heating the polymer to form ester crosslinks between the pendant hydroxyl and carboxyl groups. In the current invention the dimodal crosslinkers advantageously are added homogeneously to the polymerization mixture at the start of the process. Preferred dimodal crosslinkers include hydroxyethyl (meth)acrylate, polyethylene glycol 400 monomethacrylate, glycidyl methacrylate. Hydroxyethyl (meth)acrylate is an example of a more preferred dimodal crosslinker. Mixtures of dimodal crosslinkers can be employed.

Combinations of crosslinkers can be employed. The total amount of all crosslinkers present is sufficient to provide a polymer with good absorptive capacity, good absorption under load, and a low percent of extractable materials. Preferably the crosslinkers are present in an amount of 1,000 parts per million or more by weight based on the amount of the polymerizable monomer present, more preferably 2,000 ppm or more and most preferably 4,000 ppm or greater. Preferably, the crosslinkers are present in an amount of 50,000 parts per million or less by weight based upon the amount of the polymerizable monomer present, more preferably in amounts of 20,000 ppm or less and most preferably 15,000 ppm or less.

In those embodiments of the invention that utilize a blend of polyvinyl crosslinkers with non-vinyl and or dimodal crosslinkers, the effect on heat-treated capacity of all three types of crosslinkers is additive in nature. That is, if the amount of one crosslinker is increased the amount of another must be decreased to maintain the same overall heat-treated capacity. In addition, the proportion of the crosslinker components within the blend may be varied to achieve different polymer properties and processing characteristics. In particular the polyvinyl crosslinkers are typically more expensive than non-vinyl or dimodal crosslinkers. Therefore, the overall cost of the polymer is reduced if a greater proportion of the crosslinker blend is composed of less expensive non-vinyl and or dimodal crosslinkers. However, the non-vinyl and dimodal crosslinkers function essentially as latent crosslinkers. That is, the crosslinking imparted to the polymer by these agents is essentially not developed or seen until after a heat-treatment step. Little if any toughness is added to the hydrogel immediately after polymerization by use of such latent crosslinkers. This is an important concern for those processes for which a "tough" gel is desirable.

If too little of the total crosslinker blend is composed of polyvinyl crosslinker the polymerized hydrogel may not have sufficient toughness to be easily ground, processed, and dried. For this reason the proportion of polyvinyl crosslinker in the total crosslinker blend is preferably at least sufficient to produce a hydrogel that has enough toughness to be readily ground, processed, and dried. This toughness is inversely proportional to the centrifuged capacity of the polymer after drying but before heat-treatment. The exact amount of polyvinyl crosslinker required in the blend to achieve this level of toughness will vary, but is enough to provide a centrifuged absorption capacity of the polymer after drying but before heat-treatment of at least 10 g/g and preferably 45 g/g or less, more preferably 40 g/g or less, and most preferably 35 g/g or less.

Conventional additives which are well known in the art such as surfactants may be incorporated into the polymerization mixture. Polymerization can be accomplished under polymerization conditions in an aqueous or nonaqueous polymerization medium or in a mixed aqueous/nonaqueous polymerization medium. Polymerization accomplished by processes which employ nonaqueous polymerization media may use various inert hydrophobic liquids which are not miscible with water, such as hydrocarbons and substituted hydrocarbons including halogenated hydrocarbons as well as liquid hydrocarbons having from 4 to 20 carbon atoms per molecule including aromatic and aliphatic hydrocarbons, as well as mixtures of any of the aforementioned media.

In one embodiment, the polymer particles are prepared by contacting the monomers and crosslinkers of the invention in an aqueous medium in the presence of a free radical or oxidation reduction (redox) catalyst system and optionally a chlorine- or bromine-containing oxidizing agent under conditions such that a crosslinked hydrophilic polymer is prepared. As used herein, the term "aqueous medium" means water, or water in admixture with a water-miscible solvent. Such water-miscible solvents include lower alcohols and alkylene glycols. Preferably the aqueous medium is water.

The monomers and crosslinkers are preferably dissolved, dispersed or suspended in a suitable polymerization medium, such as, for example, the aqueous medium, at a concentration level of 15 percent by weight or greater, more preferably 25 percent or greater, and most preferably 29 percent or greater. The monomers and crosslinkers are preferably dissolved, dispersed or suspended in the aqueous medium.

Another component of the aqueous medium used to prepare the superabsorbent polymers comprises a free radical initiator, which may be any conventional water soluble polymerization initiator including, for example, peroxygen compounds such as sodium, potassium and ammonium peroxodisulfates, caprylyl peroxide, benzoyl peroxide, hydrogen peroxide, cumene hydroperoxide, tertiary butyl diperphthalate, tertiary butyl perbenzoate, sodium peracetate and sodium percarbonate. Conventional redox initiator systems can also be utilized, which are formed by combining the foregoing peroxygen compounds with reducing agents, such as, for example, sodium bisulfite, sodium thiosulfate, L- or iso-ascorbic acid or a salt thereof or ferrous salts. The initiator can comprise up to 5 mole percent based on the total moles of polymerizable monomer present. More preferably the initiator comprises from 0.001 to 0.5 mole percent based on the total moles of polymerizable monomer in the aqueous medium. Mixtures of initiators can be employed.

In one embodiment of the invention, a chlorine- or bromine-containing oxidizing agent is added to the monomer mixture or to the wet hydrogel in order to reduce the amount of residual monomers in the final polymer. It is preferably added to the monomer mixture. Preferred oxidizing agents are bromates, chlorates and chlorites. Preferably a chlorate or bromate salt is added. The counterion of the bromate or chlorate salt can be any counterion which does not significantly interfere in the preparation of the polymers or their performance. Preferably, the counterions are alkaline earth metals ions or alkali metal ions. More preferred counterions are the alkali metals, with potassium and sodium being even more preferred. Chlorine-containing oxidizing agents are preferred.

The chlorine- or bromine-containing oxidizing agent is present in a sufficient amount such that after heat-treatment the desired balance of polymer properties is achieved. If too much of the oxidizing agent is used, the ultimate properties of the polymers are degraded. If an insufficient amount is added, the above-described property improvements do not occur and the absorptive capacity will be low. Preferably, 10 ppm by weight or greater of a chlorine- or bromine-containing oxidizing agent based on the total weight of monomers (a), (b) and (c) is added, more preferably 50 ppm or greater and even more preferably 100 ppm or greater and most preferably 200 ppm or greater. Desirably, the amount of a chlorine- or bromine-containing oxidizing agent added is 2000 ppm or less by weight based on the total weight of monomers (a), (b) and (c), more desirably 1000 ppm or less, preferably 800 ppm or less and most preferably 500 ppm or less. The chlorine- or bromine-containing oxidizing agent is preferably dissolved or dispersed in the polymerization mixture prior to initiation of the polymerization. However, it may also be applied as an aqueous solution to the hydrogel, together with or in addition to the silver ions or colloidal silver.

The process of the invention may be performed in a batch manner wherein all of the reaction materials are contacted and the reaction proceeds, or it may take place with the continuous addition of one or more of the components during the reaction period. The polymerization mixture in the polymerization medium is subjected to polymerization conditions which are sufficient to produce the water-absorbent polymer.

Preferably, the reaction is performed under an inert gas atmosphere, for example, under nitrogen or argon. The reaction may be performed at any temperature at which polymerization occurs, preferably 0° C. or greater, more preferably 25° C. or greater and most preferably 50° C. or greater. The reaction is conducted for a time sufficient to result in the desired conversion of monomer to crosslinked hydrophilic polymer. Preferably, the conversion is 85 percent or greater, more preferably 95 percent or greater and most preferably 98 percent or greater. Advantageously, initiation of the reaction occurs at a temperature of at least 0° C.

It is also possible to prepare the polymer of the current invention with the addition of recycled "fines" to the polymerization mixture. See U.S. Pat. No. 5,342,899. The amount of fines added to the polymerization mixture is preferably less than 12 weight percent based on the amount of monomer in the polymerization mixture, more preferably less than 10 weight percent, and most preferably less than 8 weight percent.

It is also possible to carry out the polymerization process using multiphase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. Polymerization occurs in the aqueous phase, and suspensions or emulsions of this aqueous phase in an organic solvent permit better control of the exothermic heat of polymerization and further provide the flexibility of adding one or more of the aqueous reaction mixture components in a controlled manner to the organic phase.

Inverse suspension polymerization procedures are described in greater detail in Obayashi et al., U.S. Pat. No. 4,340,706; Flesher et. al. U.S. Pat. No. 4,506,052; and Stanley et al. U.S. Pat. No. 5,744,564. When inverse suspension polymerization or inverse emulsion polymerization techniques are employed, additional ingredients such as surfactants, emulsifiers and polymerization stabilizers may be added to the overall polymerization mixture. When any process employing organic solvent is utilized, it is important that the hydrogel-forming polymer material recovered from such processes be treated to remove substantially all of the excess organic solvent. Preferably, the hydrogel-forming polymers contain no more than 0.5 percent by weight of residual organic solvent.

During polymerization, the polymer of the invention generally absorbs all of the aqueous reaction medium to form a hydrogel. The polymer is removed from the reactor in the form of an aqueous hydrogel. The term "hydrogel" as used herein refers to water swollen superabsorbent polymer or polymer particles. In preferred embodiments, hydrogels coming out of the reactor comprise 15 to 50 percent by weight polymer, with the remainder comprising water. In a more preferred embodiment the hydrogel comprises 25 to 45 percent polymer. The hydrogel is preferably processed into a particulate shape during the polymerization reaction process in the reactor by the agitator to facilitate the removal of the hydrogel from the reactor. Preferred particle sizes of the hydrogel range from 0.001 to 25 cm, more preferably from 0.05 to 10 cm. In multiphase polymerization, the superabsorbent polymer hydrogel particles may be recovered from the reaction medium by azeotropic distillation and/or filtration followed by drying. If recovered by filtration, then some means of removing the solvents present in the hydrogel must be used. Such means are commonly known in the art.

The polymer of the invention may be in the form of particles or other forms, such as fibers.

After removal from the reactor, the hydrogel polymer is subjected to comminution, such as, for example, by a convenient mechanical means of particle size reduction, such as grinding, chopping, cutting or extrusion. The size of the gel particles after particle size reduction should be such that homogeneous drying of the particles can occur. Preferred particles sizes of the hydrogel range from 0.5 to 3 mm. This particle size reduction can be performed by any means known in the art which gives the desired result. Preferably, the particle size reduction is performed by extruding the hydrogel.

The silver ions or colloidal silver may be added to the polymerization mixture during polymerization or prior to the beginning of the polymerization, or to the crosslinked hydrogel prior to, during or after comminution but prior to drying the dried hydrogel. The presence of silver ions or colloidal silver in the water-absorbent polymer particles prior to the drying step (III) determines the effects on residual monomer, regardless of the method by which the silver ions or colloidal silver were incorporated to water-absorbent polymer particles. When the silver ions or colloidal silver are added to the polymerization mixture prior to the beginning of, or during polymerization, or to the crosslinked hydrogel prior to, during, or after comminution, followed by a drying step, the silver ions or colloidal silver are distributed substantially uniformly through the water-absorbent polymer particle rather than surfaces. Preferably, the silver ions or colloidal silver are added as an aqueous solution to the polymerization mixture prior to polymerization or to the wet hydrogel that enters the dryer prior to drying, resulting in water-absorbent polymer particles with excellently improved, low residual monomer. It is also within the scope of the present invention to add the silver ions or colloidal silver at several stages in the process, for example, both prior to and after the comminution step, as long as the addition is before any substantial degree of water moisture is removed. If the hydrogel is substantially dried prior to the application of the silver ions or colloidal silver a significant reduction of the monomer content in the polymer particles is not seen.

It is preferred to distribute the silver ions or colloidal silver substantially uniformly through the hydrogel prior to drying of the dried hydrogel. The mixing of the polymerization mixture and the silver ions or colloidal silver can be done by employing simple mixing devices. When the silver ions or colloidal silver are added to the wet polymer gel, additional mixing measures may be applied to improve the distribution of the silver ions or colloidal silver within the hydrogel. Suitable mixing methods are exemplified by stirring, kneading and agitating. It is preferred to add the silver ions or colloidal silver prior to the committing step since intensive mixing inherently occurs during committing the hydrogel to particles.

When an aqueous silver salt solution is used, it is preferably sprayed on the crosslinked hydrogel. The concentration of the silver salt solution is not critical, as long as sufficient distribution of the silver salt within the hydrogel can be ensured. Desirable concentrations of the silver salt in water range from 0.01 to 20 weight percent. The amount of water used to prepare the silver salt solution advantageously ranges from 0.1 to 999 parts by weight, based on one hundred parts by weight of dry polymer.

If an aqueous solution of a chlorine- or bromine-containing oxidizing agent is added to the hydrogel this may be applied in a similar manner as the solution comprising silver ions or colloidal silver, that is, it may be contacted with the hydrogel prior to or after comminution, together with the silver salt or as a separate solution. The preferred concentration of the chlorine- or bromine-containing oxidizing agent in water is from 0.1 to 10 weight percent.

If the solution comprising silver ions or colloidal silver is applied to the hydrogel after comminution, further components selected from water-insoluble fine inorganic or organic particles, surfactants, organic solvents, organic mineral oil and mixtures thereof may be added to avoid sticking and/or improve flow properties of the gel particles and/or to achieve better distribution of the silver salt. If the silver ions or colloidal silver are applied prior to comminution step (II), the addition of those additives is not necessary and it is preferred to contact the solution comprising silver ions or colloidal silver with the hydrogel in absence of any of those additives since the incorporation of additives may have a negative impact on absorbent polymer properties.

The silver ions or colloidal silver may also be added to the hydrogel in the form of rehydrated and swollen "fines" pretreated with an aqueous silver solution. In yet another embodiment silver-free hydrogel is combined with silver-treated superabsorbent polymer. The silver-treated superabsorbent polymer can be normally-sized material or can be "fines" or mixture of these. "Fines" are fine water-absorbent polymer particles that are created from drying, grinding and natural attrition during transport and heat-treating process of the typical gel process. The fine particle size fraction is in general undesirably small and therefore not suitable for incorporation in personal care articles such as diapers, as described in U.S. Pat. No. 5,342,899. This fine particle size fraction is often small enough to create dusting problems in production and is a source of performance deterioration due to the well-known gel blocking tendency upon initial wetting. In this specific embodiment, "fines" are understood as water-absorbent polymer particles which preferably pass through a 45 mesh (350 micrometer) screen and on contact with the solution comprising silver ions or colloidal silver the dry small polymer particles of the fines rehydrate and swell. The silver salt treated rehydrated and swollen fines particles are then thoroughly mixed with the crosslinked hydrogel obtained in step (I) of the present process. It is preferred to use 0.1 to 25 parts by weight of fines rehydrated with a solution comprising preferably 1 to 10,000 ppm and even more preferably 10 to 1,000 ppm by weight of silver ions or colloidal silver, respectively, all based on weight of dry polymer, in 0.1 to 999 parts by weight water, based on hundred parts by weight of dry polymer.

After contact with the silver ions or colloidal silver, preferably in combination with a chlorine- or bromine-containing oxidizing agent, and comminution of the hydrogel to particles, the hydrogel is subjected to drying conditions in step (III) to remove the remaining polymerization medium and any dispersing liquid including the optional solvent and substantially all of the water. Desirably, the moisture content of the polymer after drying is between zero and 20 weight percent, preferably between 5 and 10 weight percent.

The temperature at which the drying takes place is a temperature high enough such that the polymerization medium and liquid including water and optional solvent is removed in a reasonable time period, yet not so high so as to cause degradation of the polymer particles, such as by breaking of the crosslink bonds in the polymer. Preferably, the drying temperature is 180° C. or less. Desirably, the temperature during drying is 100° C. or above, preferably 120° C. or above, and more preferably 150° C. or above.

The drying time should be sufficient to remove substantially all of the water and optional solvent. Preferably, a minimum time for drying is 10 minutes or greater, with 15 minutes or greater being preferred. Preferably, the drying time is 60 minutes or less, with 25 minutes or less being more preferred. In a preferred embodiment, drying is performed under conditions such that water, and optional solvent, volatilizing away from the absorbent polymer particles, is removed. This can be achieved by the use of vacuum techniques or by passing inert gases or air over or through the layers of polymer particles. In a preferred embodiment, the drying occurs in dryers in which heated air is blown through or over layers of the polymer particles.

Preferred dryers are fluidized beds or belt dryers. Alternatively, a drum dryer may be used. Alternatively, the water may be removed by azeotropic distillation. Such techniques are well known in the art.

During drying, the superabsorbent polymer particles may form agglomerates and may then be subjected to comminution, such as, for example, by mechanical means for breaking up the agglomerates. In a preferred embodiment, the superabsorbent polymer particles are subjected to mechanical particle reduction means. Such means can include chopping, cutting and/or grinding. The object is to reduce the particle size of the polymer particles to a particle size acceptable in the ultimate end use. In a preferred embodiment, the polymer particles are chopped and then ground. The final particle size is preferably 2 mm or less, more preferably 0.8 mm or less. Preferably the particles have a size of 0.01 mm or greater, more preferably 0.05 mm or greater. Dried superabsorbent polymer particles of the present invention can be used as the basis polymer for further surface crosslinking treatment, for example, using polyvalent cations like aluminum ions and/or using one of the crosslinkers mentioned above by coating and subsequent heating at elevated temperatures.

In a preferred embodiment after drying and optional particle size reduction, the polymer particles are subjected to a heat-treatment step. Heat-treatment of the polymer provides a beneficial increase in the absorption under load (AUL) of the water-absorbent polymer, particularly the AUL under higher pressures. Suitable devices for heat-treatment include, but are not limited to, rotating disc dryers, fluid bed dryers, infrared dryers, agitated trough dryers, paddle dryers, vortex dryers, and disc dryers. One of ordinary skill in the art would vary the time and temperature of heat-treatment as appropriate for the heat transfer properties of the particular equipment used.

The time period and temperature of the heat-treatment step are chosen such that the absorption properties of the polymer are improved as desired. The polymers are desirably heat-treated at a temperature of 170° C. or above, more desirably 180° C. or above, preferably at 200° C. or above and most preferably at 220° C. or above. Below 170° C. no improvement in the absorption properties is seen. The temperature should not be so high as to cause the polymers to degrade. Preferably, the temperature is 250° C. or below and more preferably 235° C. or below. The polymers are heated to the desired heat-treatment temperature and preferably maintained at such temperature for 1 minute or more and more preferably 5 minutes or more and most preferably 10 minutes or more. Below 1 minute no improvement in properties is generally seen. If the heating time is too long it becomes uneconomical and there is a risk that the polymer may be damaged. Preferably polymer particles are maintained at the desired temperature for 60 minutes or less, preferably 40 minutes or less. Above 60 minutes no significant improvement in properties is noticed. The properties of the polymer particles can be adjusted and tailored by adjustment of the temperature and the time of the heating step.

The polymers are heated to the desired heat-treatment temperature and preferably maintained at such temperature for 1 minute or more and more preferably 5 minutes or more and most preferably 10 minutes or more. Below 1 minute no improvement in properties is generally seen. If the heating time is too long it becomes uneconomical and there is a risk that the polymer may be damaged. Preferably polymer particles are maintained at the desired temperature for 60 minutes or less, preferably 40 minutes or less. Above 60 minutes no significant improvement in properties is noticed.

The properties of the polymer particles can be adjusted and tailored by adjustment of the temperature and the time of the heating step.

After heat-treatment the polymer particles may be difficult to handle due to static electricity. It may be desirable to rehumidify the particles to reduce or eliminate the effect of the static electricity. Methods of humidification of dry polymers are well known in the art. In a preferred mode, the dry particles are contacted with water vapor. The dry particles are contacted with a sufficient amount of water to reduce or eliminate the effects of the static electricity, yet not so much so as to cause the particles to agglomerate. Preferably, the dry particles are humidified with 0.3 percent or more by weight of water and more preferably 5 percent or more by weight of water. Preferably, the dry particles are humidified with 10 percent or less by weight of water and more preferably 6 percent or less by weight of water. Optionally, agglomeration prevention or rehydration additives may be added to the crosslinked hydrophilic polymer. Such additives are well known in the art and include surfactants and inert inorganic particles such as silica; see, for example, U.S. Pat. Nos. 4,286,082; 4,734,478; and DE 2706135. Remoisturization can also be accomplished using certain salt solutions as taught in EP 0 979 250.

During and/or after the remoisturization step the dried and optionally heat-treated polymer particles may be contacted with a solution containing a dust control agent, for example a propoxylated polyol as described in U.S. Pat. Nos. 6,323,252 and 5,994,440. The propoxylated polyols are particularly suitable to bind the fine dust of the final superabsorbent polymer particles without causing agglomeration, and to bind the fine particles of powdery additives on the surface. The addition of the propoxylated polyol further results in a more homogeneous distribution of aqueous additives on the surface of the superabsorbent polymer. Exemplary propoxylated polyols are available from The Dow Chemical Company under the brand name VORANOL. The propoxylated polyol is advantageously used in an amount of from 500 to 2,500 ppm, based on the weight of dry polymer. The concentration of the propoxylated polyol in water preferably ranges from 1 to 10 weight percent and more preferably from 3 to 6 weight percent.

Other additives to which some odor control function is attributed may be used in addition to the silver salt. The additional additives may be added to the dried and optionally heat-treated polymers prior to, simultaneously with or after, the addition of the silver salt solution or colloidal silver. Exemplary additives are activated carbon, chlorophyllin, chelating agents, soda, sodium bicarbonate, copper sulfate, copper acetate, zinc sulfate, silicates, clay, cyclodextrin, citric acid, chitosan, ion exchange resin particles or combinations thereof. Synthetic or natural zeolites may also be used in addition to the silver ions or colloidal silver whereby the zeolite is not pretreated with the silver salt, that is, the zeolite is not ion exchanged with the silver cations.

To increase the flowability of the dried and optionally heat-treated polymer particles, silicon dioxide, preferably famed silica, or other fine inorganic or organic powders may be mixed with the polymer particles. Powdery additives are desirably added to and mixed with the polymer particles together with the fumed silica. The fumed silica is preferably used in amounts of from 0.01 to 5 weight percent, and more preferably from 0.05 to 3 weight percent, all based on dry polymer. An exemplary fumed silica is Aerosil R972, available from Degussa AG, Germany. The additives may be added dry or in dispersed form, such as in the form of an aqueous dispersion.

The polymers according to the present invention have a low level of residual monomers due the treatment of a solution containing silver ions or colloidal silver. A considerable advantage of the present process is that the silver ions or colloidal silver provides a beneficial decrease in residuals in both heat-treated and non-heat-treated polymers than obtainable when the process is conducted without silver treatment. It is believed that heating the polymers normally increases the amount of residual monomers due to thermally induced cleavage via a reverse Michael reaction. However, silver-treated polymers show a lower level of residuals compared with that observed when the polymer is heat-treated without the silver treatment.

The water-absorbent polymers of this invention can be used in any use wherein absorption and binding of aqueous fluids is desired and is especially suitable for such applications where it would be desirable to inhibit the development of malodor. In a preferred embodiment, the superabsorbent polymer particles of this invention are mixed into or attached to a structure of absorbent material such as synthetic or natural fibers or paper-based woven or nonwoven fibers to form a structure. In such a structure the woven or nonwoven structure functions as a mechanism for wicking and transporting fluid via capillary action to the superabsorbent polymer particles which bind and retain such fluids. Examples of such structures are sanitary napkins, diapers, and adult incontinence structures. In addition, there are various applications of the superabsorbent polymers with odor control property in non-personal care applications, for example, in medical care, agriculture, horticulture, gardening, pet litter, fertilizer, packaging and food packaging.

The absorbent structures according to the present invention comprise means to contain the superabsorbent polymer particles having odor control property. Any means capable of containing the described superabsorbent polymer particles, which means is further capable of being positioned in a device such as an absorbent garment, is suitable for use in the present invention. Many such containment means are known to those skilled in the art. For example, the containment means may comprise a fibrous matrix such as an airlaid or wetlaid web of cellulosic fibers, a meltblown web of synthetic polymeric fibers, a spunbonded web of synthetic polymeric fibers, a coformed matrix comprising cellulosic fibers and fibers formed from a synthetic polymeric material, airlaid heat-fused webs of synthetic polymeric material or open-celled foams. In one embodiment, it is preferred that the fibrous matrix comprise less than 10 preferably less than 5 weight percent of cellulosic fibers. Further, the containment means may comprise a support structure, such as a polymeric film, on which the superabsorbent polymer particles is affixed. The superabsorbent polymer particles may be affixed to one or both sides of the support structure which may be water-pervious or water-impervious.

The absorbent structures according to the present invention are suited to absorb many fluids including body fluids such as, for example, urine, menses, and blood and are suited for use in absorbent garments such as diapers, adult incontinent products and bed pads; in catamenial devices such as sanitary napkins and tampons; and in other absorbent products such as, for example, wipes, bibs and wound dressings. Accordingly, in another aspect, the present invention relates to an absorbent garment comprising an absorbent structure as described above.

SPECIFIC EMBODIMENTS OF THE INVENTION

The following examples are included to illustrate the invention, and do not limit the scope of the claims. All parts and percentages are by weight unless otherwise stated.

Particle Size Distribution (PSD) Analysis of Fines

Fines used for preparation of silver treated rehydrate and swollen fines (SRSF) were obtained from a commercial plant during the manufacturing processes of a superabsorbent polymer, after, when the dried and ground product was screened prior to heat-treatment (HT). The size fractions of the fines materials used were evaluated 8 times. The results for the particle size distribution of the fines are given below in Table 1.

TABLE 1

| | Particle Size Distribution of Fines | | | |
|---|---|---|---|---|
| No. | Particle Size Distribution (percent) | | | |
| of Evaluation | >0.315 mm | >0.212 mm | >0.150 mm | <0.150 mm |
| 1 | 0.3 | 1.8 | 20.8 | 77.1 |
| 2 | 0.2 | 2.1 | 21.0 | 76.7 |
| 3 | 0.3 | 2.0 | 19.8 | 77.9 |
| 4 | 0.3 | 1.8 | 21.1 | 76.8 |
| 5 | 0.4 | 2.1 | 20.1 | 77.4 |
| 6 | 0.3 | 2.0 | 21.7 | 75.8 |
| 7 | 0.3 | 2.2 | 22.9 | 74.6 |
| 8 | 0.3 | 2.0 | 22.5 | 75.2 |

Silver Salt Solution Treatment

Silver salt solutions were prepared before the experiments were carried out. The desired amount of silver salt was dissolved in water, then the silver salt solution was sprayed onto hydrogels in a tray, while the mixture was mixed by hand. In some cases, the gel was shaken during the spraying in a plastic container or in a vinyl bag. This simple spraying and mixing process helped to mix silver solution and gel sufficiently prior to gel mincing. The resulting silver solution treated gel was then minced by a laboratory extruder (a household mincer, MADO GmbH, Germany) through the die plate (6 mm die size) and the silver treated and minced gel was then dried in the forced-air laboratory oven (HERAEUS) at 170° C. for two hours.

Preparation and Treatment of Silver Treated Rehydrated and Swollen Fines

Silver treated rehydrated and swollen fines (SRSF) were prepared by mixing the appropriate silver salt solution with fines, which swelled quickly upon rehydration. The SRSF were mixed so that a homogeneous SRSF paste was obtained. The desired amount of gel was then mixed with the SRSF. A treated gel was obtained by mincing the gel/SRSF mixture in a laboratory extruder through the die plate (6 mm die size), followed by drying in the laboratory oven (HERAEUS) at 170° C. for two hours.

Heat-Treatment Procedure

Heat-Treatment Method 1: 20 g of polymer sample (30/50 mesh size fraction) were put into a 10 cm diameter aluminum tray and placed in a forced-air oven (HERAEUS) that had been pre-heated to the desired temperature for the desired time.

Heat-Treatment Method 2: In some experiments, the heating was performed by pre-heating a zone with a hot air-gun (laboratory fluid bed). Once the target temperature was reached and stabilized, approximately 20 g of polymer sample (30/50 mesh size fraction) were placed in the zone and a contact thermometer was placed in contact with the sample. The temperature of the sample was monitored until it stabilized at the target temperature. The sample was maintained at the target temperature for the desired time.

Method for Evaluation of Residual Monomer

The samples of the powder superabsorbent polymer prior to and after heat treatment, having a particle size fraction between (30 to 50 mesh), were used for analysis for residual monomer content. In the examples that follow, residual monomer concentrations were measured in ppm (parts per million) based on weight of dry polymer. The term "before heat-treatment" referred to the properties of the polymer after drying and sizing but before any heat-treatment (HT). The term "after heat-treatment" referred to the properties of the polymer after heat-treatment.

To determine the amount of residual acrylic acid 1.000 g of each sample was shaken for 16 hours in 185 g of an aqueous 0.9 percent NaCl solution. The slurries then were passed through a Watman No. 3 filter paper. A sample of the filtrate was injected into a liquid chromatograph and then monomeric acrylic acid was analyzed using UV detection at 205 nm. The residual monomer was calculated by comparing the peak area of the acrylic acid peak to that of a standard sample.

EXAMPLES

In all of the following experiments, the control sample was the corresponding polymer without silver salt addition. All examples marked as * were comparative experiments and not examples of the present invention.

Examples 1 to 8

Silver Salt Solution Addition to Monomer Mix Prior to Polymerization and the Effect of Chlorate Examples 1 to 8 illustrate the effect of silver salt solution treatment on residuals for gels that were polymerized in the laboratory, and also show the chlorate effect. The silver salt effect on the residual monomer content was shown in the presence (Examples 1 to 4) or absence of the chlorate (Examples 5 to 8).

Polymerization Using Laboratory Glass Reactor

Using the recipes given in Table 2, superabsorbent polymer hydrogels were made containing a chlorate level of 263 ppm (chlorate recipe, based on the total weight of acrylic acid, HETMPTA and PEG 600) or 0 ppm chlorate (non-chlorate recipe). Polymerizations were conducted using the laboratory glass reactor (reactor volume of 300 ml) without agitation. The polymerization procedures are further described below. The detailed recipes of the both trials are given below in Table 2. The degree of neutralization for both recipes was 68 percent.

TABLE 2

Polymerization Recipe containing Chlorate and No Chlorate

| Component | Conc. (aq.) percent wt. | Chlorate Recipe Weight (g) | Non Chlorate Recipe Weight (g) |
|---|---|---|---|
| Acrylic acid | 99 | 439.07 | 439.07 |
| Sodium hydroxide | 20 | 829.36 | 829.36 |
| Water | | 212.15 | 213.31 |
| HE-TMPTA[1] | 100 | 1.32 | 1.32 |
| PEG 600[2] | 100 | 1.32 | 1.32 |
| VERSENEX 80[3] | 40.2 | 0.55 | 0.55 |
| Hydrogen peroxide | 15 | 1.05 | 1.05 |
| Sodium Chlorate | 10 | 1.16 | 0.00 |
| Sodium peroxodisulfate | 10 | 7.46 | 7.46 |
| Ascorbic Acid | 1 | 6.59 | 6.59 |

[1]Highly ethoxylated trimethylopropane triacrylate
[2]Polyethylene glycol with an average molecular weight of 600 g/mol, available from Clariant Company.
[3]Pentasodium salt of diethylene triamine pentaacetic acid Preparation of Monomer Mix 299.57 g of acrylic acid were added to 829.36 g of the 20 wt percent aqueous sodium hydroxide solution in a plastic beaker which was cooled with ice. Addition of acrylic acid was added portion-wise so that the temperature did not exceed 30° C. 0.55 g VERSENEX 80 (Trademark of The Dow Chemical Company, pentasodium salt of diethylene triamine pentaacetic acid, 40.2 wt percent) was added to the pre-neutralized mix. 212.15 g of deionized water was poured into the mix. The pre-mix was put into a beaker. 1.32 g HE-TMPTA as vinyl crosslinker was dissolved in 139.5 g acrylic acid and put in the monomer mix. 1.32 g polyethylene glycol (PEG 600), used as a non-vinyl crosslinker, was dissolved in the mix. For the recipe containing chlorate, 1.16 g of 10 wt percent sodium chlorate solution was added to the monomer mix. If no chlorate was added to the mix, 1.16 g of deionized water were used instead. After every addition the mix was stirred well.

Polymerization Using Laboratory Glass Reactor 250 g of the monomer mixture were placed in a 300 ml round bottom flask equipped with a flange at the top. The flange was sealed with a lid which contained four openings, the first two of which were reserved for the thermometer and the nitrogen gas supply, one opening was connected to the vent system and the fourth one was sealed with a septum. The monomer mixture was purged for 30 minutes with a nitrogen stream (150 liter/h) to remove traces of oxygen. The corresponding amount of silver salt was added as a 0.1 wt percent silver nitrate solution to the monomer mix directly. The nitrogen bubbling was reduced (50 liter/h), and the initiators were added to the prepared monomer mix in following sequences: 1.05 g of 15 wt percent hydrogen peroxide solution, 7.46 g of 10 wt percent sodium peroxodisulfate, and 6.59 g of 1 wt percent ascorbic acid solution.

The polymerization was started at room temperature. After introduction of ascorbic acid at the start temperature, the monomer mix became slightly turbid. The mix started to gel and was more cloudy three minutes after initiation. Gel formation was seen at approximately 50° C., and the gel still appeared slightly turbid. After the temperature reached 50° C., the gel became slightly transparent. It took ca. 20-25 minutes until the polymerization mix reached 70° C., regardless of the presence of chlorate. When the temperature reached 70° C., the flask was placed in a water-bath for 60 minutes at 70° C. The reactor was then opened and a mass of aqueous polymer gel (one gel piece) was collected and was subsequently cut into small pieces, followed by mincing in a laboratory extruder having a die diameter of 6 mm. The extruded gel was dried in a forced-air laboratory oven at 170° C. for two hours. For the control and comparative samples, minced gel was dried without silver treatment. The dried materials were ground using a laboratory grinder (household mixer, Moulinette) and sieved using 30 and 50 mesh sieves. Approximately 20 g of the fraction were heat-treated in the laboratory fluid bed (heat-treatment method 2) at different temperatures as given in Table 3 for 30 minutes. Samples (30/50 mesh) were analyzed for residuals both for before and after heat treatment.

TABLE 3

Silver Salt Solution Addition to Monomer Mix and Heat Treatment Conditions

| Example | Chlorate | Silver Salt Agent | Amount of Silver Salt Agent (AgNO$_3$) in g (Ag$^+$ in ppm[a]) | Heat Treatment: Temperature (° C.)/ Time (minutes) |
|---|---|---|---|---|
| 1[C*] | 263 ppm | None | — | 190, 200 and 220° C./30 minutes |
| 2 | 263 ppm | AgNO$_3$ | 0.0014 g (10 ppm Ag$^+$) | 190, 200 and 220° C./30 minutes |
| 3 | 263 ppm | AgNO$_3$ | 0.0070 g (50 ppm Ag$^+$) | 190, 200 and 220° C./30 minutes |
| 4 | 263 ppm | AgNO$_3$ | 0.0140 g (100 ppm Ag$^+$) | 190, 200 and 220° C./30 minutes |
| 5[C*] | 0 ppm | none | — | 190, 200 and 220° C./30 minutes |
| 6 | 0 ppm | AgNO$_3$ | 0.0014 g (10 ppm Ag$^+$) | 190, 200 and 220° C./30 minutes |
| 7 | 0 ppm | AgNO$_3$ | 0.0070 g (50 ppm Ag$^+$) | 190, 200 and 220° C./30 minutes |
| 8 | 0 ppm | AgNO$_3$ | 0.0140 g (100 ppm Ag$^+$) | 190, 200 and 220° C./30 minutes |

[C]control sample
[a]silver ion concentration in ppm = parts per million of dry polymer

TABLE 4

Residual Monomer Concentrations for Gel Polymerization with Silver Salt Solution Treatment before and after Heat Treatment (HT)

Residual Monomer Concentration (ppm[a])

| Example | After Drying | After HT at 190° C. | After HT at 200° C. | After HT at 220° C. |
|---|---|---|---|---|
| 1[C*] | 259 | 417 | 409 | 380 |
| 2 | 221 | 421 | 425 | 500 |
| 3 | 193 | 235 | 249 | 245 |
| 4 | 193 | 241 | 264 | 192 |
| 5[C*] | 379 | n.d. | 561 | 652 |
| 6 | 264 | n.d. | 379 | 431 |
| 7 | 216 | n.d. | 375 | 428 |
| 8 | 197 | n.d. | 363 | 394 |

[C]control sample
[a]ppm = parts per million of dry polymer
n.d. Not determined

The results of Examples 1 to 8 in Table 4 clearly show the effect of silver ion on the residual monomer when added to the monomer mix prior to polymerization. Polymerization with a silver salt solution resulted in highly improved residual monomer levels after drying, regardless of the presence of chlorate. Polymerization of the non-chlorate recipe resulted in higher residual monomer than that of the chlorate recipe. Therefore, the use of a silver salt in the presence of the chlorate in the polymerizing monomer mix clearly showed an advantage compared to the non-chlorate recipe with regard to the residual monomer values. Examples 1 to 8 also show that the silver salt solution treatment of the monomer mix prior to polymerization provided significantly improved residual monomer levels in the polymer particles over that of the control product, when heat treated at high temperatures, regardless of the presence of chlorate. However, the positive effect of the silver salt treatment on residual monomers upon heat-treatment was more profound when used in combination with chlorate.

Example 9

Feed Polymer Gel and Control Sample

The improved superabsorbent polymer products of the present invention were prepared by adding silver salt solution to gel prepared using the recipe given in Table 2 ("chlorate recipe").

Batch polymerization was carried out using a kneader type stainless steel reactor having a stainless steel agitator assembly and a high torque stirring motor with gear reducers. This assembly allowed grinding of the gel formed during polymerization. After a polymerization time of 30 minutes, conversion was almost complete and was at least about 99 percent. The polymers absorbed the aqueous solution and formed an aqueous hydrogel. The water-swollen superabsorbent hydrogel removed from the reactor was taken prior to gel mincing for the experiments 9 to 21 in Table 5 below. The hydrogel was not sticky and was tough enough that it could be handled easily in the form of small particulate gel pieces and was treated as described in the following examples.

The control sample (Example 9) was prepared by mincing the non-extruded hydrogel using a laboratory mincer through the die plate (6 mm die size) and subsequently drying it in a laboratory oven (HERAEUS) at 170° C. for two hours. The dried materials were ground using a laboratory grinder (household mixer, Moulinette) and sifted using a 30 and a 50 mesh sieve (that is, particle size distribution between 0.595 mm and 0.297 mm). 20 g of the polymer particles were placed in aluminum tray and heat-treated in an air-forced laboratory oven at 180, 200 and 220° C. for 60 minutes (heat-treatment method 1). The resulting heat-treated samples were evaluated for residual monomers. The results for residual monomers are given in Table 6.

Examples 10 to 15

Silver Salt Solution Treatment and Processing of the Hydrogel with Silver Solution Example 10 was a comparative sample and was not silver salt treated. Examples 11 to 15 (Table 5) relate to the treatment of gel with silver salt aqueous solution form. In Examples 11 to 15 the amounts of the treatment agents indicated in Table 5 were dissolved in 180 g of water. The solutions were sprayed on 2,000 g gel of Example 9 and mixed thoroughly by hand. The silver salt solution treated gel was then minced by a laboratory mincer through the die plate (6 mm die size) and the silver salt solution treated and minced gel was then dried in the laboratory oven (HERAEUS) at 170° C. for two hours. The dried materials were further ground, sifted and heat-treated as described under the same conditions described in Example 9. The results for residual monomers were given in Table 6.

Examples 16 to 21

Treatment of the Hydrogel with Silver Treated Rehydrated Swollen Fines (SRSF)

Example 16 was a comparative sample and was not silver salt treated. Examples 17 to 21 (Table 5) relate to the treatment of gel with silver salt treatment in the form of rehydrated and swollen fines. The silver salt treated and rehydrated and swollen fines (SRSF) were prepared by adding the corresponding amounts of silver salt (Table 5) dissolved in 180 g of water with 20 g of dry fines. The resulting SRSF were added to 2,000 g of non-extruded gel samples of Example 9 and mixed thoroughly by hand. The SRSF treated gel was then minced by a laboratory mincer through the die plate (6 mm die size) and the silver treated and minced gel was then dried in the laboratory oven (HERAEUS) at 170° C. for two hours. The dried materials were further ground, sifted and heat-treated as described under the same conditions described in Example 9. The results for residual monomers are given in Table 6.

TABLE 5

Gel Treatment using Silver Salt Solution and Silver Salt Treated Rehydrated and Swollen Fines (SRSF)

| Example | Agent/ Treatment | Amount of AgNO$_3$ (ppm$^a$) | Amount of water | Amount of fines |
|---|---|---|---|---|
| 9$^{C*}$ | none | None | none | none |
| 10* | none | None | 180 g water | none |
| 11 | AgNO$_3$/ solution$^{(1)}$ | 0.025 g AgNO$_3$ (Ag$^+$ = 22 ppm | 180 g water | none |
| 12 | AgNO$_3$/ solution | 0.05 g AgNO$_3$ (Ag$^+$ = 44 ppm) | 180 g water | none |
| 13 | AgNO$_3$/ solution | 0.1 g AgNO$_3$ (Ag$^+$ = 88 ppm) | 180 g water | none |
| 14 | AgNO$_3$/ solution | 0.15 g AgNO$_3$ (Ag$^+$ = 132 ppm) | 180 g water | none |
| 15 | AgNO$_3$/ solution | 0.20 g AgNO$_3$ (Ag$^+$ = 176 ppm) | 180 g water | none |
| 16* | none | None | 180 g water | 20 g fines |
| 17 | AgNO$_3$/fines$^{(2)}$ | 0.025 g AgNO$_3$ (Ag$^+$ = 22 ppm | 180 g water | 20 g fines |
| 18 | AgNO$_3$/fines | 0.05 g AgNO$_3$ (Ag$^+$ = 44 ppm) | 180 g water | 20 g fines |
| 19 | AgNO$_3$/fines | 0.1 g AgNO$_3$ (Ag$^+$ = 88 ppm) | 180 g water | 20 g fines |
| 20 | AgNO$_3$/fines | 0.15 g AgNO$_3$ (Ag$^+$ = 132 ppm) | 180 g water | 20 g fines |
| 21 | AgNO$_3$/fines | 0.20 g AgNO$_3$ (Ag$^+$ = 176 ppm) | 180 g water | 20 g fines |

$^C$control sample
$^a$ppm = silver ion concentration in parts per million of dry polymer
$^{(1)}$solution = silver ion solution treatment
$^{(2)}$fines = silver ion treatment using silver treated rehydrated and swollen fines (SRSF)

TABLE 6

Silver Salt Solution Treatment Results for Residuals before and after Heat Treatment

| Example | After Drying in ppm$^a$ | After HT at 180° C. in ppm | After HT at 200° C. in ppm | After HT at 220° C. in ppm |
|---|---|---|---|---|
| 9$^{C*}$ | 280 | 425 | 512 | 445 |
| 10* | 307 | 436 | 520 | 441 |
| 11 | 187 | 336 | 438 | 381 |
| 12 | 195 | 301 | 374 | 334 |
| 13 | 194 | 331 | 420 | 303 |
| 14 | 203 | 329 | 399 | 377 |
| 15 | 182 | 339 | 431 | 356 |
| 16* | 265 | 363 | 488 | 408 |
| 17 | 232 | 357 | 461 | 307 |
| 18 | 164 | 305 | 426 | 353 |
| 19 | 166 | 284 | 422 | 389 |
| 20 | 179 | 303 | 400 | 382 |
| 21 | 180 | 322 | 421 | 391 |

$^C$control sample
$^a$ppm = parts per million of dry polymer

It can be seen from Examples 10 to 15 in Table 6 that the silver salt solution treatment provided significantly improved amounts of residuals in the polymer particles over that of the control sample. The significant improvement was found independently of the heat-treatment. It is known in general that heating samples lead to increased residual values in all samples due to the thermally induced cleavage of the copolymerized dimer via a reverse Michael reaction yielding regenerated acrylic acid. Consequently, products with a high value of residuals were obtained. The silver salt solution treated samples showed significant improvement in residual monomer concentration.

It is clear from Examples 16 to 21 in Table 6 that the SRSF method of the present invention provided significantly improved residual monomer levels when compared to the control sample, regardless of heating. In addition, it can be seen from Table 5, comparing Examples 10 to 15 and Example 16 to 21, that the effect of adding silver salt treated rehydrated and swollen fines (SRSF) to the hydrogel was approximately the same as adding the same amount of silver salt in aqueous solution.

What is claimed is:

1. A process for the preparation of a water-absorbent polymer, which comprises: (I) polymerizing a polymerization mixture comprising: (a) one or more ethylenically unsaturated carboxyl-containing monomers, (b) one or more crossliniking agents, (c) optionally one or more comonomers copolymerizable with the carboxyl-containing monomer, and (d) a polymerization medium to form a crosslinked hydrogel, (II) comminutting the hydrogel to particles, and (III) drying the hydrogel; wherein an aqueous solution of a silver salt is added to the polymerization mixture prior to step (I) and the silver salt remains in salt form during polymerization, and the silver salt is distributed substantially uniformly throughout the water-absorbent polymer particles rather than solely on the surface of said particle.

2. The process of claim 1 further comprising (IV) heat treating the dried hydrogel after step (III).

3. The process of claim 1 wherein the silver salt is added in amount of from 1 to 10,000 ppm, based on weight of polymer solids.

4. A process for the preparation of a water-absorbent polymer, which comprises: (I) polymerizing a polymerization mixture comprising: (a) one or more ethylenically unsaturated carboxyl-containing monomers, (b) one or more crossliniking agents, (c) optionally one or more comonomers copolymerizable with the carboxyl-containing monomer, and (d) a polymerization medium, to form a crosslinked hydrogel, (II) committing the hydrogel to particles, and (III) drying the hydrogel, wherein silver ions or colloidal silver are added prior to or after comminution step (II) and prior to step (III) in the form of silver-treated rehydrated and swollen fines particles, and wherein the silver ions or colloidal silver are mixed with the hydrogel to distribute the silver ions or colloidal silver throughout the hydrogel.

5. The process of claim 4 wherein the silver ions are derived from silver acetate, silver nitrate, silver benzoate, silver bromate, silver chlorate, silver lactate, silver molybdate, silver nitrite, silver(I) oxide, silver perchlorate, silver permanganate, silver selenate, silver selenite, silver sulfadiazine, silver sulfate, or mixtures thereof.

6. The process of claim 1 wherein the aqueous solution of a silver salt is prepared by complexation of a water-insoluble silver salt.

7. The process of claim 6 wherein the water-insoluble silver salt is silver chloride or silver bromide, and the complexation agent is an alkali metal thiosulfate.

8. The process of claim 2 wherein the dried hydrogel from step (III) is heated to a temperature of from 170 to 250° C. for from 1 to 60 minutes in the heat treatment step (IV).

9. The process of claim 8 which is conducted in the presence of a chlorine- or bromine-containing oxidizing agent.

10. The process of claim 9 wherein the chlorine- or bromine-containing oxidizing agent is dissolved or dispersed in the polymerization mixture in an amount of from 10 to 2,000 ppm, based on the total weight of monomers (a), (b) and (c) prior to initiation of the polymerization in step (I).

11. The process of claim 9 wherein the chlorine- or bromine-containing oxidizing agent is selected from the group consisting of sodium chlorate, potassium chlorate, sodium bromate, potassium bromate, sodium chlorite, and potassium chlorite, or mixtures thereof.

12. The process of claim 1 wherein the carboxyl-containing monomer is selected from the group consisting of ethylenically unsaturated carboxylic acids, ethylenically unsaturated carboxylic acid anhydrides, salts of unsaturated carboxylic acids, and mixtures thereof the optional comonomer is selected from the group consisting of an acrylamide, a vinyl pyrrolidone, a vinyl sulphonic acid or a salt thereof, an acrylonitrile, a cellulosic monomer, a modified cellulosic monomer, a polyvinyl alcohol monomer, and a starch hydrolyzate monomer; and the crossliniking agent is selected from the group consisting of (i) one or more polyvinyl crossliniking agents, (ii) a mixture of one or more polyvinyl crossliniking agents and one or more non-vinyl crossliniking agents, and (iii) a mixture of one or more polyvinyl crossliniking agents and one or more dimodal crossliniking agents.

13. The process of claim 12 wherein the polyvinyl crossliniking agent is selected from the group consisting of a di- or polyester of an unsaturated mono- or polycarboxylic acid with a polyol, an unsaturated polyester obtained by reacting a polyol with an unsaturated acid, a di- or tri(meth)acrylic acid ester obtained by reacting a polyepoxide with a (meth)acrylic acid, a bis(meth)acrylamide, a carbamyl ester obtained by reacting a polyisocyanate with a hydroxyl group-containing monomer, a di- or poly(meth)allyl ether of a polyol, a di- or polyallyl ester of a polycarboxylic acid, an ester of an unsaturated mono- or polycarboxylic acid with a mono(meth)allyl ester of a polyol; and an ethylenically unsaturated compound containing at least one group reactive with carboxyl, carboxylic acid anhydride, hydroxyl, amino or amide groups.

14. The process of claim 13 wherein the polyvinyl crossliniking agent employed is a compound of the formula

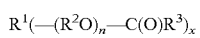

wherein
$R^1$ is a straight- or branched-chain polyalkoxy radical with 1 to 10 carbon atoms, optionally substituted with one or more oxygen atoms in the backbone, having x valences;
$R^2$ is independently in each occurrence an alkylene group of 2 to 4 carbon atoms;
$R^3$ is independently in each occurrence a straight- or branched-chain alkenyl moiety with 2 to 10 carbon atoms;
n is a number from 1 to 20;
x is a number from 2 to 8.

15. The process of claim 14 wherein $R^1$ is derived from trimethylolpropane, $R^2$ is ethylene (—$CH_2CH_2$—), $R^3$ is vinyl (—CH=$CH_2$), the average value of n is from 2 to 6, and x is 3.

16. Water-absorbent polymer prepared by the process of claim 1.

17. An absorbent structure comprising water-absorbent polymer of claim 16 and at least one of a woven or nonwoven structure of paper, synthetic fibers, natural fibers, or a combination of these.

18. The process of claim 4 wherein the carboxyl-containing monomer is selected from the group consisting of ethylenically unsaturated carboxylic acids, ethylenically unsaturated carboxylic acid anhydrides, salts of unsaturated carboxylic acids and mixtures thereof; the optional comonomer is selected from the group consisting of an acrylamide, a vinyl pyrrolidone, a vinyl sulphonic acid or salt thereof, an acrylonitrile, a cellulosic monomer, a modified cellulosic monomer, a polyvinyl alcohol monomer and a starch hydrolyzate monomer; and the crossliniking agent is selected from the group consisting of (i) one or more polyvinyl crossliniking agents, (ii) a mixture of one or more polyvinyl crossliniking agents and one of more non-vinyl crossliniking agents, and (iii) a mixture of one or more polyvinyl crossliniking agents and one of more dimodal crossliniking agents.

19. The process of claim 1, wherein the water-absorbent polymer has a residual monomer content of 500 ppm or less.

20. The process of claim 1, wherein the water-absorbent polymer has a residual monomer content of 400 ppm or less.

21. The process of claim 4, wherein the water-absorbent polymer has a residual monomer content of 500 ppm or less.

22. The process of claim 4, wherein the water-absorbent polymer has a residual monomer content of 400 ppm or less.

23. The process of claim 1, wherein the wherein the silver ions are derived from silver acetate or silver nitrate.

* * * * *

UNITED STATES PATENT AND TRADEMARK OFFICE
CERTIFICATE OF CORRECTION

PATENT NO.         : 7,312,268 B2
APPLICATION NO. : 10/469664
DATED                : December 25, 2007
INVENTOR(S)      : Young-Sam Kim It is certified that error appears in the above-identified patent and that said Letters Patent is hereby corrected as shown below:

Column 11,
Line 40, "the committing step" should be replaced by -- the comminuting step --.

Line 41, "during committing the" should be replaced by -- during comminuting the --.

Column 22,
Line 49, "crossliniking" should be replaced by -- crosslinking --.

Line 51, "crossliniked" should be replaced by -- crosslinked --.

Line 52, "comminutting" should be replaced by -- comminuting --.

Column 23,
Line 1 claim 4, "crossliniking" should be replaced by -- crosslinking --.

Line 3 claim 4, "crosslini-" should be replaced by -- crosslin- --.

Line 43 claim 12, "thereof" should be replaced by -- thereof; --.

Line 49 claim 12, "crosslini-" should be replaced by -- crosslin- --.

Line 51 claim 12, "crossliniking agents and one or more non-vinyl crossliniking" should be replaced by -- crosslinking agents and one or more non-vinyl crosslinking --.

Line 53 claim 12, "crossliniking agents and one or more dimodal crossliniking" should be replaced by -- crosslinking agents and one or more dimodal crosslinking --.

Line 56 claim 13, "crossliniking" should be replaced by -- crosslinking --.

Column 24,
Line 9 claim 14, "crossliniking" should be replaced by -- crosslinking --.

Line 25 claim 15, "($—CH^2CH^2—$)" should be replaced by -- ($—CH_2CH_2—$) --.

Line 26 claim 15, "($—CH=CH^2$)" should be replaced by -- ($—CH=CH_2$) --.

Line 43 claim 18, "crossliniking" should be replaced by -- crosslinking --.

UNITED STATES PATENT AND TRADEMARK OFFICE
CERTIFICATE OF CORRECTION

PATENT NO. : 7,312,268 B2
APPLICATION NO. : 10/469664
DATED : December 25, 2007
INVENTOR(S) : Young-Sam Kim It is certified that error appears in the above-identified patent and that said Letters Patent is hereby corrected as shown below:

Line 44 claim 18, "crosslini-" should be replaced by -- crosslin- --.

Line 46 claim 18, "crossliniking agents and one or more non-vinyl crossliniking" should be replaced by -- crosslinking agents and one or more non-vinyl crosslinking --.

Line 48 claim 18, "crossliniking agents and one or more dimodal crossliniking" should be replaced by -- crosslinking agents and one or more dimodal crosslinking --.

Signed and Sealed this

Fifteenth Day of July, 2008

JON W. DUDAS
*Director of the United States Patent and Trademark Office*